US012779062B2

(12) United States Patent
Yamauchi et al.

(10) Patent No.: US 12,779,062 B2
(45) Date of Patent: Nov. 3, 2026

(54) METHOD OF STERILIZING LIQUID EJECTION HEAD, AND LIQUID EJECTION HEAD ASSEMBLY

(71) Applicant: CANON KABUSHIKI KAISHA, Tokyo (JP)

(72) Inventors: Sachiko Yamauchi, Kanagawa (JP); Shinichi Sakurada, Tokyo (JP); Yoshinori Itoh, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 1003 days.

(21) Appl. No.: 17/693,844

(22) Filed: Mar. 14, 2022

(65) Prior Publication Data

US 2022/0296739 A1 Sep. 22, 2022

(30) Foreign Application Priority Data

Mar. 18, 2021 (JP) ................................ 2021-044711
Mar. 10, 2022 (JP) ................................ 2022-037248

(51) Int. Cl.

*A61L 2/07* (2006.01)
*B41J 2/165* (2006.01)
*B41J 2/175* (2006.01)

(52) U.S. Cl.

CPC ............. *A61L 2/07* (2013.01); *B41J 2/16552* (2013.01); *B41J 2/1754* (2013.01); (Continued)

(58) Field of Classification Search

CPC ....... A61L 2/07; B41J 2/16552; B41J 2/1754; B41J 2/1753; B41J 2/17553; B41J 2002/16555

See application file for complete search history.

(56) References Cited

U.S. PATENT DOCUMENTS 5,790,147 A * 8/1998 Hensel ................. B41J 2/16552 347/49
6,158,838 A * 12/2000 Capurso ............... B41J 2/16552 347/29

(Continued)

FOREIGN PATENT DOCUMENTS

JP 2001074731 A * 3/2001 ....... A61B 5/150022
JP 2004003950 A * 1/2004

(Continued)

OTHER PUBLICATIONS

FOR document and translation (Year: 2007).*

(Continued)

*Primary Examiner* — Maris R Kessel
*Assistant Examiner* — Aham Lee
(74) *Attorney, Agent, or Firm* — Venable LLP

(57) ABSTRACT

A liquid ejection head to be sterilized includes: an ejection element substrate with an ejection port surface in which an ejection port for ejecting a liquid is formed; and a liquid storage part that stores the liquid to be supplied to the ejection port. A method of sterilizing the liquid ejection head includes: covering at least the ejection port surface with a protection member in a non-contact manner; making a liquid ejection head assembly by housing the protection member and the liquid ejection head or covering the protection member's opening portion with a sheet member that is vapor permeable at least at one portion so as to block entry of bacteria into the liquid ejection head; and performing vapor sterilization on the assembly.

13 Claims, 11 Drawing Sheets

(52) U.S. Cl.
CPC .... *B41J 2002/16555* (2013.01); *B41J 2/1753* (2013.01); *B41J 2/17553* (2013.01)

(56) References Cited

U.S. PATENT DOCUMENTS

| | | | | |
|---|---|---|---|---|
| 2004/0228759 | A1* | 11/2004 | Frost | A61L 2/208 422/26 |
| 2006/0274110 | A1* | 12/2006 | Kang | B41J 2/16552 347/33 |
| 2012/0249689 | A1* | 10/2012 | Albertin | B41J 2/16552 347/85 |
| 2015/0190541 | A1* | 7/2015 | Kitamura | A61L 2/07 422/26 |
| 2019/0009540 | A1* | 1/2019 | Iwano | B41J 2/16505 |
| 2019/0061353 | A1* | 2/2019 | Shimizu | B41J 2/16508 |

FOREIGN PATENT DOCUMENTS

| | | | | | |
|---|---|---|---|---|---|
| JP | 2007160019 | A | * | 6/2007 | |
| WO | WO-9111374 | A2 | * | 8/1991 | |
| WO | WO-2013175834 | A1 | * | 11/2013 | B65B 55/14 |

OTHER PUBLICATIONS

Translation JP2001074731A (Year: 2001).*
JP 2001074731 A—description translation (Year: 2001).*
English Machine Translation of JP_2004003950_A.*
English translation of Sudo (WO 2013175834 A1). (Year: 2013).*
Itoh et al., U.S. Appl. No. 17/693,829, filed Mar. 14, 2022.
Sakurada et al., U.S. Appl. No. 17/693,836, filed Mar. 14, 2022.
Hirose et al., U.S. Appl. No. 17/693,854, filed Mar. 14, 2022.

* cited by examiner

METHOD OF STERILIZING LIQUID EJECTION HEAD, AND LIQUID EJECTION HEAD ASSEMBLY

BACKGROUND OF THE INVENTION

Field of the Invention

The present disclosure relates to a technique for performing vapor sterilization on a liquid ejection head that ejects a liquid.

Description of the Related Art

In recent years, a technique has been proposed in which a liquid ejection head including an ejection substrate with minute ejection ports formed therein is used to eject a liquid such as a cell suspension containing cells to perform a predetermined process on the liquid. In order to avoid inclusion of unnecessary bacteria into the liquid to be ejected from the liquid ejection head used in such a technique, the liquid ejection head needs to be sterilized before the liquid is filled into the liquid ejection head. At present, for the sterilization of an instrument that handles a biological object or the like, a sterilization method utilizing high-pressure steam, an ethylene oxide gas, or a gamma ray and a disinfection method utilizing an ultraviolet ray have been known. Japanese Patent Laid-Open No. 2004-3950 discloses a technique for disinfecting a liquid ejection head that ejects a biological sample with an ultraviolet ray or steam.

Usually, in a case of sterilizing an instrument that handles a biological object with high-pressure steam, in order to maintain a sterilized state even after the sterilization, the instrument is sealed in a bag which does not allow bacteria to pass therethrough and, at least at one region, has a portion which allows steam to pass therethrough, and that bag is placed in a sterilization apparatus and subjected to high-pressure steam sterilization. For example, a process performed in which the bag with the instrument sealed therein is exposed to high-pressure steam at 121° C. for 15 minutes to perform sterilization, and the inside of the sterilization apparatus is returned to normal temperature and pressure. As the inside of the sterilization apparatus is returned to normal temperature and pressure after the sterilization process, the steam generated during the sterilization transforms from a gas into a liquid, so that a liquid is produced by condensation inside the high-pressure steam sterilization apparatus and inside the bag. For this reason, a drying process of drying the bag with the instrument put therein is usually performed after the high-pressure steam sterilization step to vaporize the liquid accumulated in the bag.

SUMMARY OF THE INVENTION

By performing the drying process after performing the high-pressure steam sterilization process as described above, the liquid inside the bag can be vaporized. Here, with a metallograph, the present disclosers observed the surface of a liquid ejection head in which ejection ports were formed (ejection port surface) after performing the drying step. As a result, the present disclosers confirmed that many dried liquid marks (watermarks) were present on the ejection port surface which were formed as a result of the drying of the liquid attached to the ejection port surface. In a case where such dried liquid marks are formed on the ejection port surface, they lower the lyophobicity of the ejection port surface and make it easier for the ejected liquid to get attached to the ejection port surface, and the attached liquid may cause ejection failure at ejection ports.

A method of sterilizing a liquid ejection head according to an aspect of the present invention is a method of sterilizing a liquid ejection head including an ejection element substrate that has an ejection port surface in which an ejection port for ejecting a liquid is formed, and a liquid storage part that stores the liquid to be supplied to the ejection port, the method including: covering at least the ejection port surface of the liquid ejection head with a protection member in a non-contact manner; making a liquid ejection head assembly by housing the protection member and the liquid ejection head or covering an opening portion of the protection member with a sheet member that is vapor permeable at least at one portion in such a manner as to block entry of bacteria into the liquid ejection head; and performing vapor sterilization on the assembly.

According to the present disclosure, it is possible to properly sterilize a liquid ejection head with a vapor while also inhibiting the occurrence of ejection failure of the liquid ejection head.

Further features of the present invention will become apparent from the following description of exemplary embodiments with reference to the attached drawings.

DESCRIPTION OF THE EMBODIMENTS

Embodiments of the present disclosure will be described below in detail with reference to the drawings. In each of these embodiments, a description will be given of a method of sterilizing a liquid ejection head to be used to process a liquid such as a cell suspension containing cells, and a liquid ejection head assembly to be used in a case of implementing that sterilization method. Note that in drawings to be referred to in the following description, a Z direction represents the direction of gravity, with a Z1 direction representing the upward direction along the direction of gravity (hereinafter also referred to simply as "upward") and a Z2 direction representing the downward direction along the direction of gravity (hereinafter also referred to simply as "downward").

First Embodiment (Liquid Ejection Head)

Figure 1:
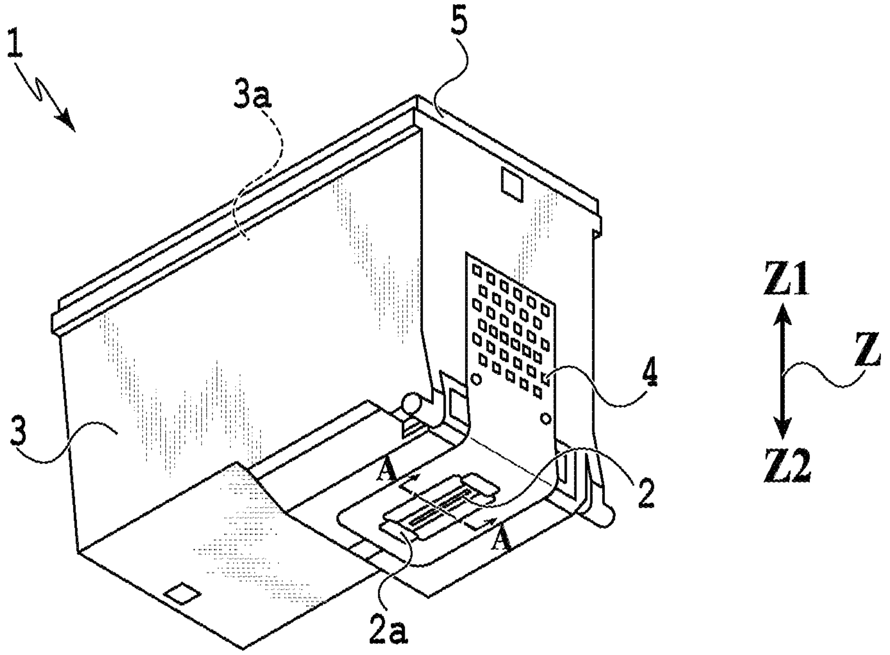
FIG. 1 is a perspective view illustrating a liquid ejection head in an embodiment.

FIG. 1 is a perspective view illustrating an embodiment of a liquid ejection head according to the present disclosure. A liquid ejection head 1 has: a housing 3 having a liquid storage part 3*a* capable of storing a liquid containing cells or the like; an ejection element substrate 2 that is provided at a bottom surface portion of the housing 3; and an electrical connector 4 that sends electrical power and control signals to the ejection element substrate 2. Also, in the present embodiment, a lid 5 that closes an opening portion of the liquid storage part 3*a* is provided in a detachable manner. The liquid storage part 3*a* is capable of holding as little as a few tens of μl of liquid to a few tens of ml of liquid.

Figure 2A:
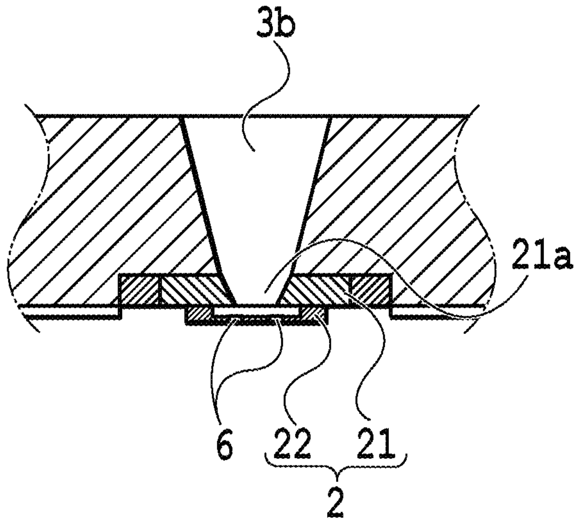
FIGS. 2A and 2B are views illustrating a structure of and around an ejection element substrate.
Figure 2B:
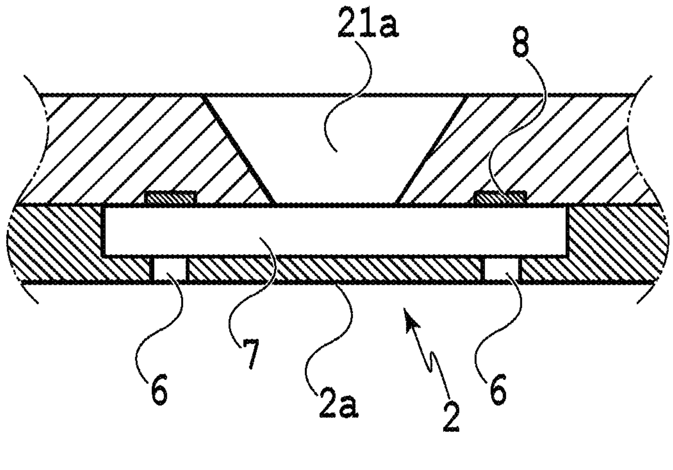

FIGS. 2A and 2B are views illustrating a structure of and around the ejection element substrate 2. FIG. 2A is a cross-sectional view along A-A line in FIG. 1, and FIG. 2B is an enlarged view illustrating a configuration around ejection ports in the ejection element substrate 2 in FIG. 2A. The ejection element substrate 2 has a silicon substrate 21 and an ejection port forming member 22 fixed to the lower surface of this silicon substrate 21. A plurality of ejection ports 6 are formed in the ejection port forming member 22. An outer surface 2*a* in which the opening portions of these ejection ports 6 are formed will be referred to as the ejection port surface 2*a* in the following description. Between the ejection port forming member 22 and the silicon substrate 21, flow channels 7 communicating with the ejection ports 6 are formed. The flow channels 7 communicate with a liquid supply port 21*a* formed in the silicon substrate 21. Further, the liquid supply port 21*a* communicates with the liquid storage part 3*a* in the housing 3 via a liquid outlet port 3*b* formed in a bottom portion of the housing 3. In this way, the liquid stored in the liquid storage part 3*a* is supplied into the flow channels 7 through the liquid outlet port 3*b* and the liquid supply port 21*a*. The liquid supplied into the flow channels 7 is filled into the plurality of ejection ports 6 formed in the ejection port forming member 22.

Moreover, the silicon substrate 21 is provided with ejection energy generation elements (hereinafter referred to as "ejection elements") 8 that generate ejection energy for ejecting the liquid from the ejection ports 6. These ejection elements 8 are disposed at positions where they respectively face the ejection ports 6. The ejection elements 8 provided in the present embodiment are each formed of an electrothermal transducer (heater) that generates thermal energy for ejecting the liquid from the ejection port 6. With the ejection elements driven by a driving circuit and control circuit not illustrated to generate thermal energy, the liquid present in the flow channels 7 is caused to undergo film boiling, and the liquid can be ejected from the ejection ports 6 with a pressure generated by the film boiling. A surface treatment has been performed on the ejection port surface 2*a* of the ejection element substrate 2 so that the ejected liquid cannot easily get attached to the ejection port surface 2*a*. For example, a treatment that imparts lyophobicity is performed. This is to inhibit a decrease in the ejection performance of the ejection ports 6 due to attachment of the liquid to the ejection port surface 2*a*. That is, in a case where the liquid gets attached to the ejection port surface 2*a*, the attached liquid obstructs the ejection of the liquid from the ejection ports 6, thereby causing ejection failure such as insufficient liquid ejection or misfiring. Lyophobicity is imparted to the ejection port surface 2*a* for this reason.

The liquid ejection head 1 can support processing of a liquid such as a cell fluid. For example, the liquid ejection head 1 can support a process such as cell processing in which a cell fluid is ejected from the liquid ejection head to thereby form holes in the surface membranes of the cells contained in the cell fluid and introduce a predetermined compound from these holes. Here, in the case of using the liquid ejection head in such a process, it is essential to sterilize the liquid ejection head and necessary to perform a sterilization process as below. Note that in this example, electrothermal transducers are used as the ejection elements but the configuration may be such that electromechanical transducers such as piezoelectric transducers are used to eject the liquid from the ejection ports. In this case too, cells contained in a liquid can be processed similarly to the case of using electrothermal transducers.

(Sterilization Process)

Sterilization is defined as reducing the number of remaining microorganisms such as bacteria and viruses to 1/1000000. At present, high-pressure steam sterilization, ethylene oxide gas sterilization, gamma ray sterilization, and so on are available as sterilization methods. High-pressure steam sterilization refers to killing microorganisms or the like via coagulation of proteins with steam generated. The sterilization conditions of high-pressure steam sterilization are, for example, heating at a temperature of 121° C. (a pressure of atomospheric pressure+0.1 MPa) for 15 minutes and at a temperature of 134° C. (a pressure of atomospheric pressure+0.2 MPa) for 10 minutes. The pressure in a high-pressure steam sterilization process is preferably atomospheric pressure+0.1 MPa or more and atomospheric pressure+0.2 MPa or less.

In order to reliably perform high-pressure steam sterilization, the inside of the liquid ejection head 1, which is a sterilization target, needs to be filled with steam with a 100% humidity (saturated steam). The flow channels 7 communicating with the ejection ports 6 have a long and narrow shape, and are each therefore one of the portions in the liquid ejection head 1 that is difficult to fill steam with 100% humidity. Thus, to fill the inside of the flow channels with steam, the ejection ports 6, which are located at the very end, are preferably open.

(Liquid Ejection Head Assemblies)

Now, configurations of liquid ejection head assemblies usable in the sterilization process of the liquid ejection head 1 will be described. Note that in the following description, in order to clarify characteristic features of liquid ejection head assemblies in the present embodiment, a liquid ejection head assembly used in a common method of sterilizing a liquid ejection head will firstly be described as a comparative example of the present embodiment, and the liquid ejection head assemblies in the present embodiment will then be described.

<Liquid Ejection Head Assembly in Comparative Example>

Figure 3A:
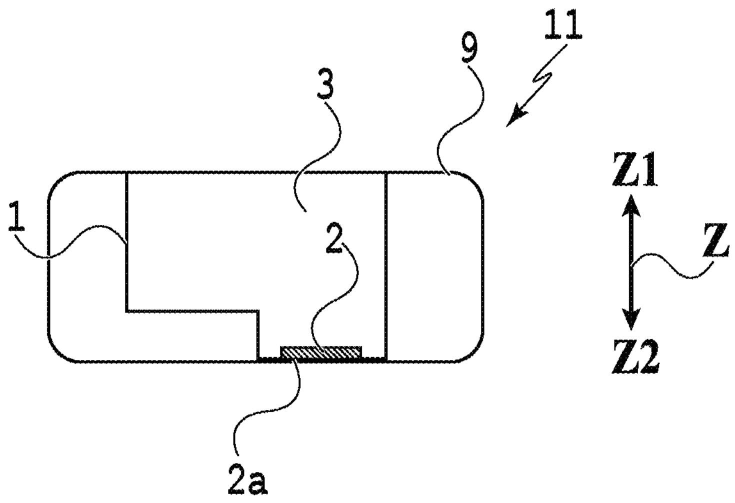
FIGS. 3A and 3B are vertical cross-sectional side views schematically illustrating a configuration of a liquid ejection head assembly in a comparative example.
Figure 3B:
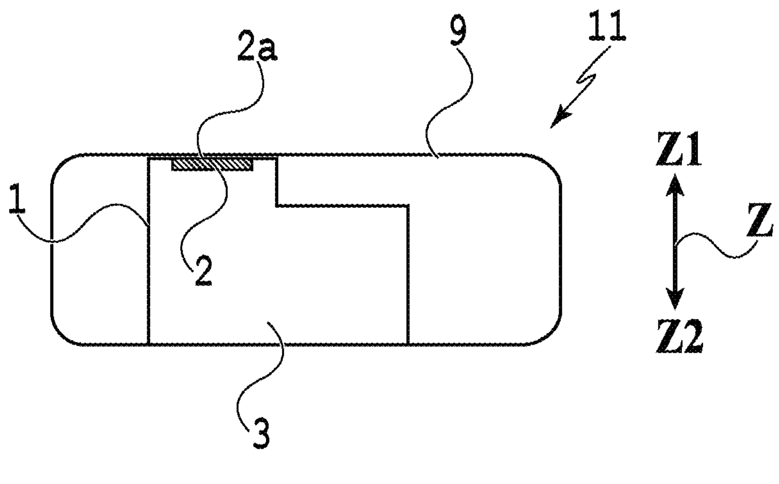

FIGS. 3A and 3B are views illustrating a configuration of a liquid ejection head assembly (hereinafter also referred to simply as "assembly") 11 in the comparative example. The assembly 11 in the comparative example includes a liquid ejection head 1 and a sheet member 9 housing the liquid ejection head 1.

<<Liquid Ejection Head>>

The liquid ejection head 1 illustrated in FIGS. 3A and 3B is similar to the liquid ejection head 1 illustrated in FIG. 1. At a bottom portion of the liquid ejection head 1, an ejection element substrate 2 with a plurality of ejection ports arrayed therein are provided, and an ejection port surface 2*a* of the ejection element substrate 2, which is its lower surface, has been processed to be lyophobic to the liquid to be ejected from the ejection ports.

<<Sheet Member>>

The sheet member 9 blocks entry of bacteria into the liquid ejection head 1 after a sterilization process of the liquid ejection head 1 to maintain the sterilized state, and is formed in a bag shape capable of housing the liquid ejection head 1. The sheet member 9 is made of a material that blocks bacterial penetration. The sheet member 9 is also made of a material that is vapor permeable at least at one portion. Thus, by placing the liquid ejection head assembly 11 in a vessel (also called "chamber") of a sterilization apparatus (also called "autoclave") and performing steam sterilization, the liquid ejection head 1 can be sterilized. After being sterilized, the liquid ejection head 1 is taken out of the sterilization apparatus in the form of the assembly 11. In this way, the liquid ejection head 1 can be maintained in the sterilized state. Note that materials to be used for the sheet member 9 forming the assembly 11 which allow neither bacteria nor vapor to pass therethrough include a polyethylene film and the like. Materials which do not allow bacteria to pass therethrough but allow vapor (gas) to pass therethrough include sterile paper, polyethylene non-woven fabric, and the like. In view of avoiding closure of the ejection ports 6 in the liquid ejection head 1 by paper dust, a material that blocks permeation of bacteria and is vapor permeable is preferably polyethylene non-woven fabric. The air permeability of the vapor permeable material is preferably 7 sec./100 ml or more and 120 sec./100 ml or less. Note that the air permeability can be measured by using the Gurley method specified in JIS P 8117.

The liquid ejection head assembly 11 in the comparative example configured as described above is placed in the sterilization apparatus and subjected to a high-pressure steam sterilization process. Now, a description will be given of a case of performing high-pressure steam sterilization in a state where the ejection port surface 2*a* of the ejection element substrate 2 of the liquid ejection head 1 housed in the bag-shaped sheet member 9 as illustrated in FIG. 3A is arranged to be situated on the lower side in the direction of gravity. In the case of performing the high-pressure steam sterilization process with such an arrangement, a liquid accumulates in an inner lower region of the assembly 11 as the inside of the sterilization apparatus is returned to normal temperature and pressure after the sterilization process. This liquid includes a liquid resulting from the condensation of steam present in the assembly 11, a liquid sucked from the outside of the assembly 11 to the inside of the assembly 11 by the depressurization from high pressure to normal pressure, and the like. The liquid having accumulated in the assembly 11 gets integrated and moved due to capillary force generated as a result of contact between the ejection element substrate 2 and the sheet member 9, and gets attached to the ejection element substrate 2.

Incidentally, the assembly 11 can be placed in the sterilization apparatus with the ejection port surface 2*a* of the liquid ejection head 1 facing up as illustrated in FIG. 3B and subjected to the high-pressure steam sterilization. In this case too, a liquid accumulates in a lower region of the assembly 11 after the sterilization process. However, since the ejection port surface 2*a* of the ejection element substrate 2 of the liquid ejection head 1 is facing up, the liquid having accumulated in the lower region of the assembly 11 is less likely to contact the ejection port surface 2*a*. Nevertheless, in this case too, the liquid may get attached to the ejection port surface 2*a*. That is, since the sheet member 9 is flexible and easily contacts the ejection port surface 2*a*, capillary force is generated at regions where the sheet member 9 and the ejection port surface 2*a* contact each other. Thus, there is a case where the liquid produced inside the assembly 11 gets integrated and moved by the capillary force and consequently gets attached to the ejection port surface 2*a*.

As described above, in the case of performing a high-pressure steam sterilization process by using the assembly 11 in the comparative example, the liquid produced inside the assembly 11 may get attached to the ejection port surface 2*a* of the ejection element substrate 2. This liquid is not pure water and contains components dissolved from the sheet member 9 and various members forming the liquid ejection head 1 during the high-pressure steam sterilization process, and the like. Even if anti-dissolution materials are selected as the sheet member 9 and members of the liquid ejection head 1, it will be difficult to completely prevent dissolution of these. For this reason, in a case where the liquid attached to the ejection port surface 2*a* after the high-pressure steam sterilization gets dried, the dissolved components and the like contained in the liquid get attached to the ejection port surface 2*a*. The present inventors assume that these become dried liquid marks (watermarks) and make it easier for the liquid to get attached to the ejection port surface 2*a*, which can be a cause of ejection failure.

<Liquid Ejection Head Assemblies in Present Embodiment>

Figure 4A:
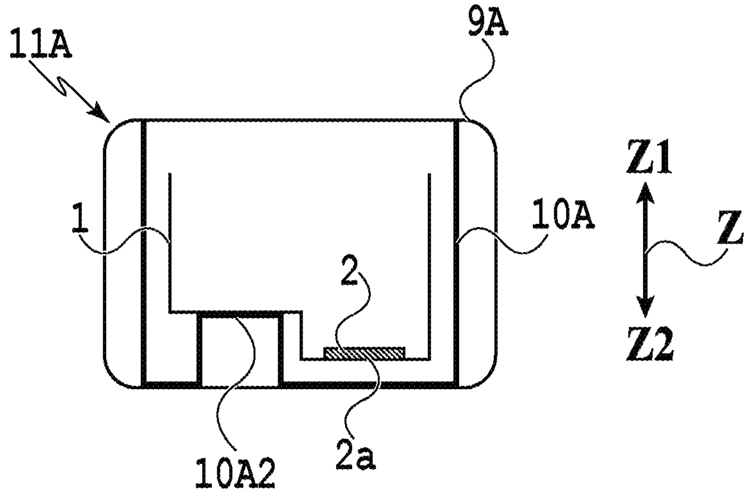
FIGS. 4A and 4B are vertical cross-sectional side views schematically illustrating a first example of an assembly in the embodiment.

Next, the liquid ejection head assemblies in the present embodiment will be described with reference to FIGS. 4A to 7A. FIG. 4A is a vertical cross-sectional side view schematically illustrating an assembly 11A (first example) in the present embodiment. The assembly 11A in this example includes a liquid ejection head 1, a sheet member 9A housing the liquid ejection head 1, and a protection member 10A supporting the liquid ejection head 1 from below and covering the ejection port surface 2*a* of the ejection element substrate 2.

Figure 5A:
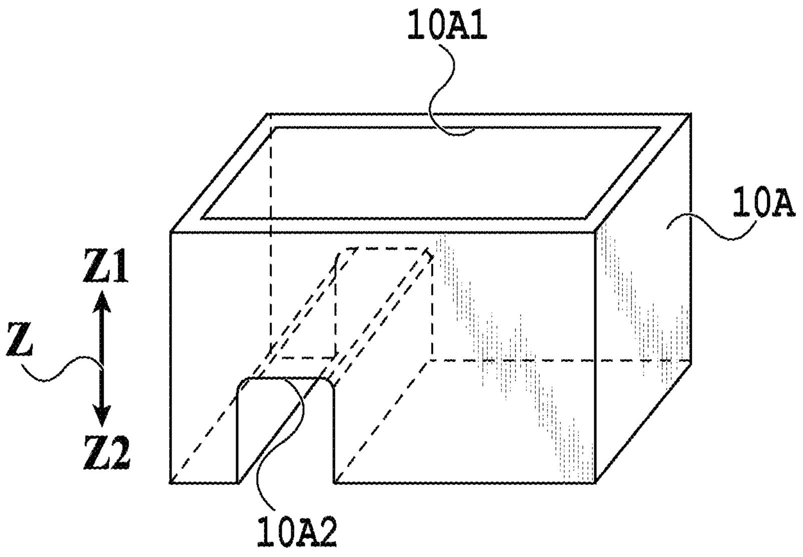
FIGS. 5A and 5B are perspective views illustrating a configuration of a protection member and a sheet member used in the liquid ejection head assembly illustrated in FIGS. 4A and 4B.
Figure 5B:
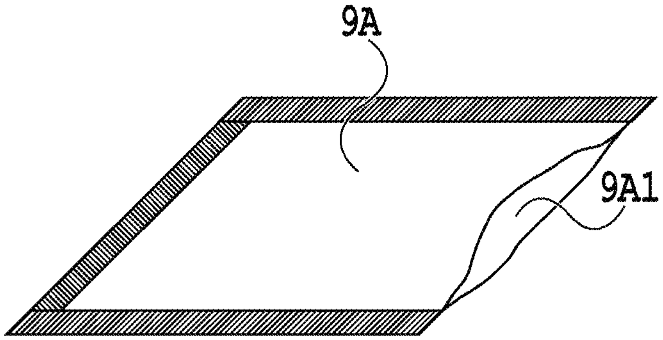

FIG. 5A is a perspective view illustrating a configuration of the protection member 10A used in the liquid ejection head assembly 11A illustrated in FIG. 4A, and FIG. 5B is a perspective view illustrating a configuration of the sheet member 9A illustrated in FIG. 4A. The protection member 10A illustrated in FIG. 5A has a hollow box shape having a housing space to house the liquid ejection head 1, and an opening portion 10A1 is formed at the top. Also, at one portion of the bottom of the protection member 10A, an inwardly protruding support portion 10A2 is formed which supports a portion of the bottom of the liquid ejection head 1 located off the ejection element substrate 2.

By housing the liquid ejection head 1 in this protection member 10A from its opening portion 10A1, the support portion 10A2 of the protection member 10A supports the portion of the bottom of the liquid ejection head 1 located off the ejection element substrate 2, since the protection member has higher rigidity than the sheet member. As a result, the liquid ejection head 1 is held with the ejection element substrate 2 separated from the protection member 10A by a predetermined interval, and the ejection port surface 2*a* of the ejection element substrate 2 is covered with the bottom portion of the protection member 10A facing it with a predetermined interval therebetween (see FIG. 4A). The Young's modulus of the protection member is preferably 1

MPa or more and 100 MPa or less. Here, the Young's modulus can be measured by following JIS K 7127:1999. Note that the protection member 10A has such a rigidity that it does not get deformed by the heat of the high-pressure steam sterilization process or the like. In particular, the softening temperature of the protection member is preferably 121° C. or more. Here, the softening temperature of the protection member can be measured by following JIS K 6863:1994. Examples of the material of the protection member include polypropylene, polyethylene terephthalate, and the like. The protection member can be made of another material as long as the material does not greatly deform during steam sterilization.

The protection member 10A housing the liquid ejection head 1 is inserted into the bag-shaped sheet member 9A as illustrated in FIG. 5B from its opening portion 9A1. Then, the opening portion 9A1 is sealed with tape or the like to tightly close the sheet member 9A. As a result, the liquid ejection head assembly 11A illustrated in FIG. 4A is made.

As with the above-described comparative example, the sheet member 9A is formed of a bag-shaped member that houses the liquid ejection head 1 and the protection member 10A such that the liquid ejection head 1 after a sterilization process can be maintained in the sterilized state. For the sheet member 9A, a material that blocks permeation of bacteria and is vapor permeable at least at one portion is used. For this reason, among the parts of the assembly 11A, the ejection element substrate 2 is exposed to the atmosphere. This is because the sheet member 9A is vapor permeable at least at one portion and the protection member 10A is held out of contact with the ejection element substrate 2.

With the liquid ejection head assembly 11A configured as described above, it is possible to properly sterilize the liquid ejection head 1 by placing the assembly 11A inside the vessel of a sterilization apparatus and performing high-pressure steam sterilization. Further, with the assembly 11A in the present embodiment, it is possible to reduce attachment of the liquid produced inside the assembly 11A after the high-pressure steam sterilization process to the ejection port surface 2*a* of the ejection element substrate 2. Specifically, in the assembly 11A in the present embodiment, the protection member 10A supports the liquid ejection head 1 in a state where the protection member 10A is separated from the ejection element substrate 2, and the sheet member 9A and the ejection port surface 2*a* of the ejection element substrate 2 are out of contact with each other. Thus, even in the case where a liquid is produced in the assembly 11A due to the inside of the vessel returning to normal temperature and pressure after the high-pressure steam sterilization process, attachment of that liquid to the ejection port surface 2*a* of the ejection element substrate 2 is inhibited which would otherwise occur due to capillary force generated by contact between the ejection element substrate 2 and the sheet member 9A. This greatly reduces attachment of the liquid to the ejection port surface 2*a*. As a result, the possibility of formation of dried liquid marks on the ejection port surface 2*a* of the liquid ejection head 1 in a state where the assembly 11A is dried drops greatly, so that the ejection performance of the liquid ejection head is maintained well.

Figure 4B:
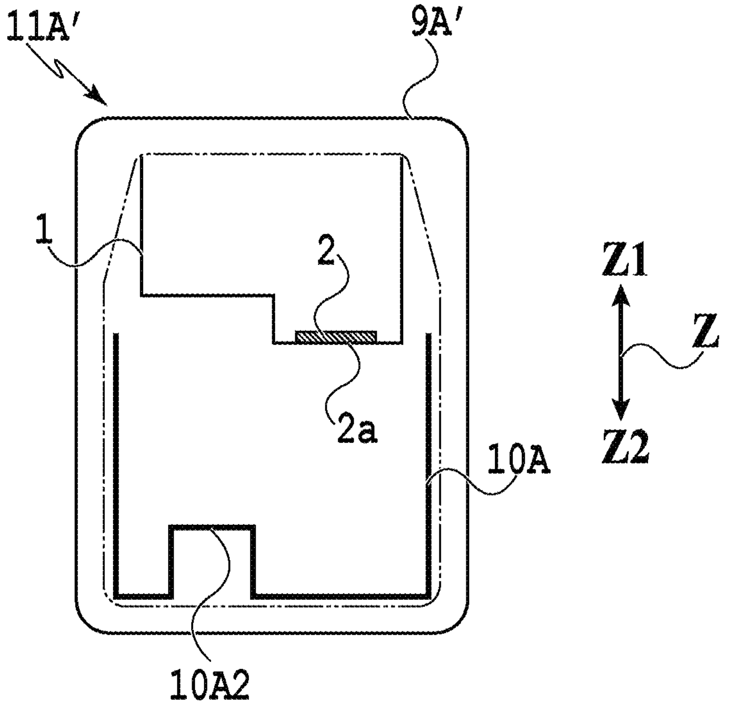

Next, a preferable size of the sheet member 9A will be described using FIG. 4B. The assembly 11A illustrated in FIG. 4A employs a configuration in which the protection member 10A is not fixed to the liquid ejection head 1. Thus, the size of the bag-shaped sheet member 9A housing the liquid ejection head 1 and the protection member 10A is preferably limited to a predetermined dimension or smaller in some cases. In the case where disposing the protection member 10A housing the liquid ejection head 1 into the sheet member 9A, the protection member 10A is disposed with its opening portion 10A1 facing the inner surface of the bag-shaped sheet member 9. Here, it is preferable to use a sheet member 9 with such a dimension that the liquid ejection head 1 does not come out of the protection member 10A from the opening portion 10A1 of the protection member 10A. Specifically, it is preferable that the peripheral length of the inner surface of the bag-shaped sheet member 9A (the length of a solid line 9A' in FIG. 4B) be less than the minimum value of a peripheral length surrounding both the liquid ejection head 1 and the protection member 10A in a state where the liquid ejection head 1 is not housed in the protection member 10A (the length of the long dashed double-short dashed line in FIG. 4B). Using the sheet member 9A with such a dimension can prevent the liquid ejection head 1 from coming out of the protection member 10A covered with the sheet member 9A. Conversely, in a case where the peripheral length of the inner surface of a bag-shaped sheet member 9A' of an assembly 11A' illustrated in FIG. 4B (the length of the solid line 9A') is greater than the minimum value of the peripheral length surrounding the protection member 10A and the liquid ejection head 1 (the length of the long dashed double-short dashed line), the liquid ejection head 1 may come out of the protection member 10A. In a case where the opening portion 10A1 of the protection member 10A is facing up, the liquid ejection head 1 is kept in the supported state inside the protection member 10A by gravity. In this way, the protection member 10A does not come of the liquid ejection head 1. However, in a case where the opening portion 10A1 faces down due to transportation of the assembly 11A' or the like, the liquid ejection head 1 may come out of the protection member 10A. For this reason, by setting the dimension of the sheet member 9A to be used as described above, it is possible to prevent the liquid ejection head 1 from coming out of the protection member 10A without having to pay attention to the orientation of the opening portion 10A1 of the protection member 10A.

Figure 6A:
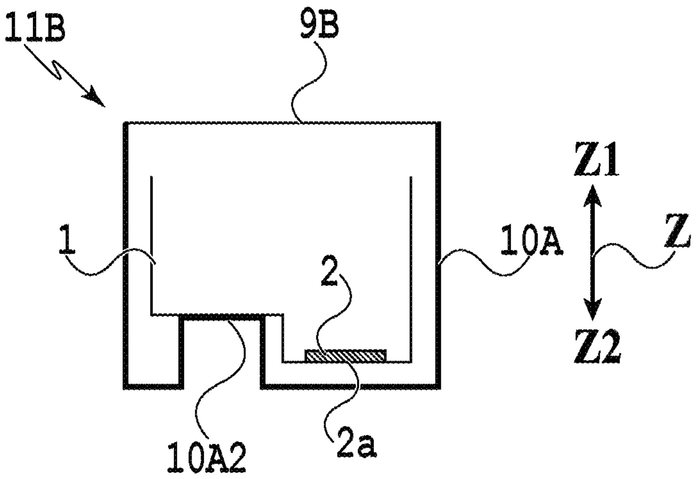
FIGS. 6A and 6B are vertical cross-sectional side views illustrating second and third examples of the assembly in the embodiment.

Also, in the case of employing a configuration in which the protection member 10A is not fixed to the liquid ejection head 1 as described above, an assembly 11B (second example) as illustrated in FIG. 6A can be made. Specifically, the assembly 11B has a configuration in which a sheet member 9B is fixed to the opening portion 10A1 of the protection member 10A by thermocompression bonding or the like. In this example too, the sheet member 9B is made of a material which has a function of blocking permeation of bacteria and is vapor permeable at least at one portion.

Figure 6B:
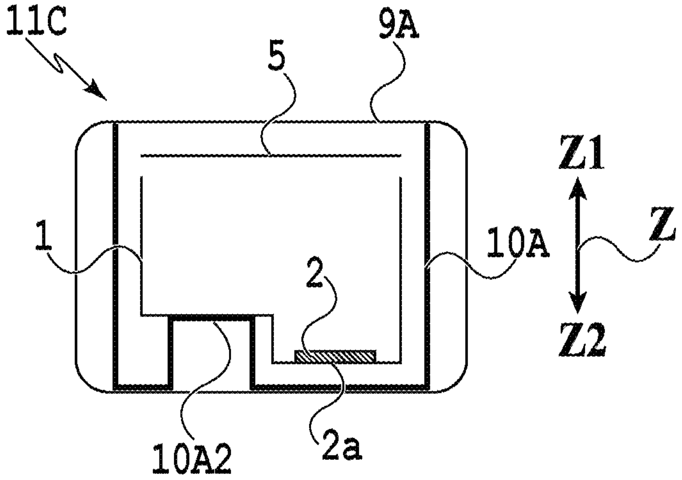

Also, as an assembly employing a configuration in which the protection member 10A is not fixed to the liquid ejection head 1, an assembly 11C (third example) as illustrated in FIG. 6B can be made. This assembly 11C has a configuration including the liquid ejection head 1, the protection member 10A, and the sheet member 9A as well as the lid 5 at the opening portion of the liquid storage part 3*a* of the liquid ejection head 1. With this assembly 11C, it is easier to take out the sterilized liquid ejection head 1. Specifically, in a case of using the sterilized liquid ejection head 1, the user firstly rips the bag-shaped sheet member 9A inside a clean bench. Next, from the ripped portion of the sheet member 9A, the user takes out the protection member 10A, in which the liquid ejection head 1 and the lid 5 are inserted, with one hand, and turns the protection member 10A upside down toward the other hand. In this way, the user can easily take out the liquid ejection head 1 along with the lid 5. Here, since the opening portion of the liquid storage part 3*a* is covered with the lid 5, the inside of the liquid storage part 3*a* does not get contaminated. Moreover, since the user's hand does not contact the ejection port surface 2*a* of the ejection element substrate 2, neither the ejection port surface 2*a* nor the ejection ports 6 get contaminated.

The protection member 10A can also function to protect the electrical connector. Since the protection member 10A is a hollow box shape, it can protect most part of the liquid ejection head and protect the liquid ejection head from external damage. Further, the protection member 10A can also prevent breakage of the sheet member 9A by the liquid ejection head 1.

Figure 7A:
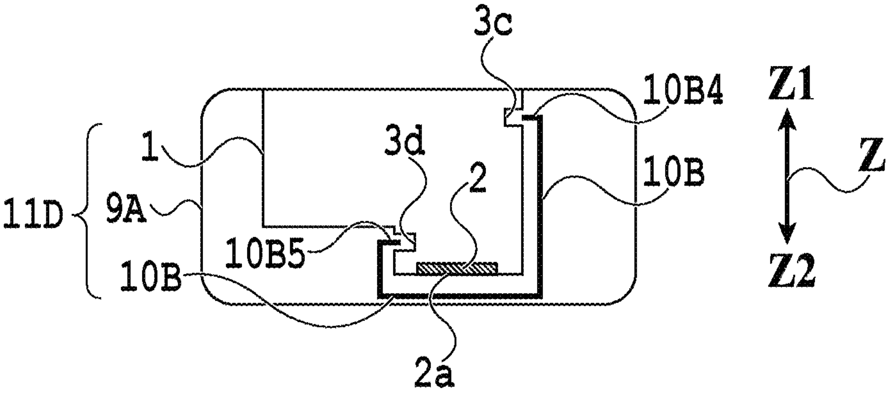
FIG. 7A is a vertical cross-sectional side view illustrating a fourth example of the assembly in the embodiment.
Figure 7B:
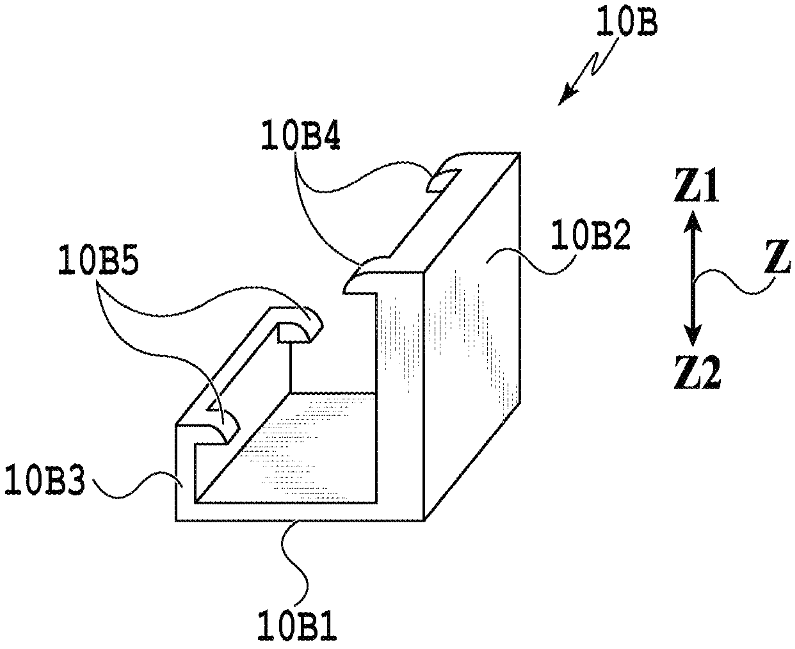
FIG. 7B is a perspective view of the protection member illustrated in FIG. 7A.

Next, an assembly 11D (fourth example) will be described based on FIGS. 7A and 7B. FIG. 7A is a vertical cross-sectional side view schematically illustrating the assembly 11D, and FIG. 7B is a perspective view illustrating a protection member 10B used in the assembly 11D.

The liquid ejection head assembly 11D illustrated in FIG. 7A includes the liquid ejection head 1, the protection member 10B made of a resin and detachably fixed to the housing 3, which forms the outer shell of the liquid ejection head 1, and the sheet member 9A. As illustrated in FIG. 7B, the protection member 10B is formed in a bent shape by a bottom portion 10B1 and two side portions 10B2 and 10B3 rising from the bottom portion 10B1. At the upper ends of the two side portions 10B2 and 10B3, inwardly protruding claws (engagement portion) 10B4 and 10B5 are formed. The claws 10B4 are engageable with recesses 3*c* formed in one side portion of the housing 3, and the claws 10B5 are engageable with recesses 3*d* formed in the opposite side portion of the housing 3. By engaging these claws 10B4 and 10B5 respectively with the corresponding recesses 3*c* and 3*d* in the housing 3, the protection member 10B can be detachably fixed to the housing 3.

In the state where the protection member 10B is fixed to the housing 3, the bottom portion 10B1 of the protection member 10B functions as a covering portion covering the ejection element substrate 2, which is provided at the bottom of the housing 3, with a predetermined interval therebetween. Since the protection member 10B is made of a resin, the resin's elasticity enables the recesses 3*c* and 3*d* and the claws 10B4 and 10B5 be disengaged from one another and thus enables the protection member 10B to be detached from the housing 3.

After the protection member 10B is fixed to the liquid ejection head 1, the liquid ejection head 1 is put into the bag-shaped sheet member 9A and the opening portion of the sheet member 9A is tightly closed. As a result, the assembly 11D is made. In this assembly 11D too, since the ejection port surface 2*a* of the ejection element substrate 2 is covered with the protection member 10B, the ejection port surface 2*a* does not contact the sheet member 9A. This greatly lowers the possibility of attachment of the liquid produced inside the assembly 11D after the sterilization process to the ejection port surface 2*a*. Thus, it is possible to properly perform steam sterilization while inhibiting a decrease in the ejection performance of the liquid ejection head 1. Also, in the case of employing a configuration like this example in which the protection member 10B is fixed to the liquid ejection head 1, the size of the bag-shaped sheet member 9A to be used can be freely selected as long as it is a size that can house the liquid ejection head 1 with the protection member 10B fixed thereto.

With the assemblies 11A to 11D described above, the protection members 10A and 10B each having a box shape or a bent shape have been shown. Note, however, that the shape of the protection member is not limited to these shapes. The protection member can employ another shape as long as it is a shape that can cover the ejection port surface 2*a* of the ejection element substrate 2 without contacting the ejection port surface 2*a*. For example, the ejection port surface 2*a* may be covered in non-contact manner with a planar protection member. Alternatively, a rib-shaped protrusion may be provided on a side surface or bottom surface of a box-shaped protection member and a portion of the liquid ejection head (excluding the ejection element substrate) may be hooked on this protrusion. In this way, the ejection port surface of the ejection element substrate can be covered in a non-contact manner with the bottom surface of the protection member. Also, the shape, structure, and material of the protection member can be selected as appropriate with the use conditions, application, life, cost, and so on taken into account.

Also, the protection member may be made in such a shape that the sterilized liquid ejection head can be easily detached from the protection member in a case of using the liquid ejection head. For example, in the case of a protection member having a hollow box shape, the protection member may be formed such that spaces where fingers can be inserted are formed between the protection member and the liquid ejection head, in order to make it easier to grasp the liquid ejection head with fingers.

<Sterilization Method>

Next, a method of performing vapor sterilization on the liquid ejection head in one of the above-described assemblies will be described. In the present embodiment, a high-pressure steam sterilization process using steam is performed as the vapor sterilization process. The sterilization target (in this example, the liquid ejection head assembly) is put into the vessel of a sterilization apparatus capable of this high-pressure steam sterilization process, and the door of the sterilization apparatus is closed to close the vessel. Steam is generated inside the vessel or steam is externally introduced into the vessel to set the inside of the vessel at a high temperature and pressure. Instead of the above, a high-pressure steam sterilization apparatus that reduces the air inside its vessel with a vacuum pump to introduce steam into the vessel may be employed. After the sterilization target is sterilized by setting the inside of the vessel at a high temperature and pressure for a certain time, the inside of the vessel is returned to normal temperature and pressure. Methods of returning the inside of the vessel to normal temperature and pressure include ventilation and natural heat dissipation, as well as a method involving forcibly ventilating the vessel by using a vacuum pump and a method involving forcibly lowering the temperature by spraying water from the top of the vessel.

In the case of the method of forcibly returning the inside to normal temperature and pressure, the temperature inside the assembly drops abruptly, so that the pressure inside the assembly becomes negative pressure. As a result, a liquid present outside the assembly may pass through the sheet member's sterile paper and enter the inside of the assembly. In the case of forcible ventilation using a vacuum pump, too, the pressure drop by the ventilation causes the temperature to drop drastically, so that the steam is condensed and a liquid is produced inside the assembly.

Thereafter, the assembly placed in the vessel is dried. Some high-pressure steam sterilization apparatuses are capable of performing processes from sterilization to drying. Also, after the high-pressure steam sterilization, the sterilization target (assembly) may be taken out of the high-pressure steam sterilization apparatus and dried in a dryer.

In the sterilization of the liquid ejection head, as mentioned earlier, one of the liquid ejection head assemblies 11A to 11D is made, and the one of the assemblies 11A to 11D is put into the high-pressure steam sterilization apparatus to be sterilized. Here, in the present embodiment, contact between the ejection port surface 2*a* of the ejection element substrate 2 and the sheet member 9A or 9B can be prevented with the protection member 10A or 10B. Accordingly, integration and movement of a liquid to the ejection port surface 2*a* of the ejection element substrate 2 by capillary force between the ejection port surface 2*a* and the sheet member 9A or 9B can be prevented. This can greatly lower the possibility of attachment of the liquid to the ejection port surface 2*a*.

Figure 8A:
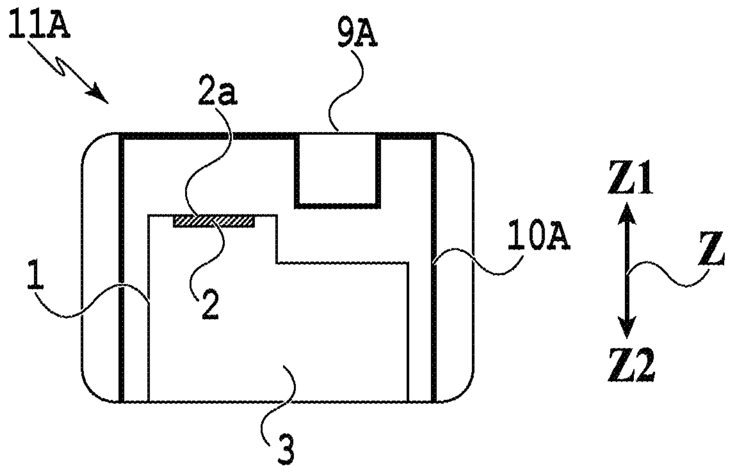
FIGS. 8A and 8B are vertical cross-sectional side views illustrating a state where an assembly is placed in a vessel with an ejection port surface facing up.
Figure 8B:
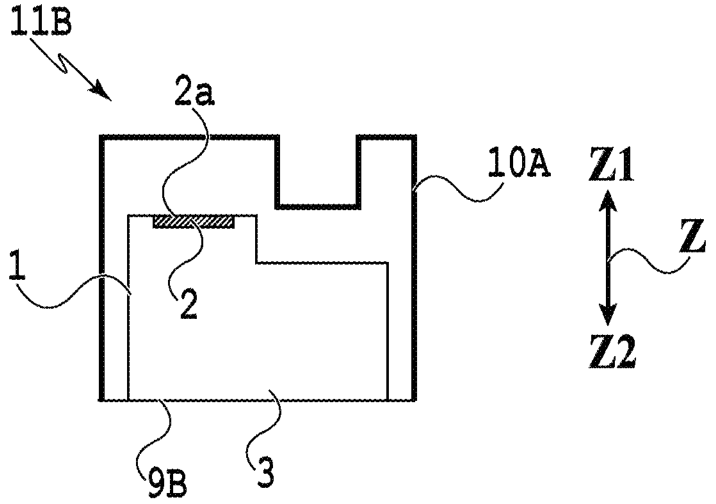

Depending on the steam sterilization conditions (temperature, pressure, and cooling means), the liquid is easily produced inside the assembly placed in the vessel. Thus, it is more preferable to place the assembly 11A or 11B in the vessel of the high-pressure steam sterilization apparatus with the ejection port surface 2*a* of the ejection element substrate 2 facing up, as illustrated in FIG. 8A or 8B. "Facing up" here refers to such an orientation that, in the state where the assembly is placed, the direction of liquid ejection from the ejection ports 6 of the ejection element substrate 2 (liquid ejection direction) is within a range from the horizontal direction to the exactly upward direction (vertically upward direction). On the other hand, "facing down" refers to such an orientation that, in the state where the assembly is placed, the liquid ejection direction is within a range from the horizontal direction to the exactly downward direction (vertically downward direction). Note that while only the assemblies 11A and 11B are illustrated in FIGS. 8A and 8B, it is likewise preferable that the other assemblies 11C and 11D be placed in the vessel with the ejection port surface 2*a* facing up. By placing the assembly with the ejection port surface 2*a* facing up as described above, it is possible to lower the possibility of attachment of the liquid to the ejection port surface 2*a*.

As described above, with the liquid ejection head assemblies in the present embodiment, even in the case of performing high-pressure steam sterilization as the sterilization method, it is possible to reduce attachment of the liquid to the ejection port surface 2*a* of the ejection element substrate 2. Note that the assemblies 11A to 11D in the present embodiment are applicable not only to a high-pressure steam sterilization process but also to other sterilization processes. For example, the assemblies 11A to 11D in the present embodiment are also applicable to a case of using a sterilization method in which a gas is used during the sterilization and a liquid is produced after the sterilization. In any of the sterilization processes, by using the assemblies 11A to 11D in the present embodiment, it is possible to properly perform the sterilization process on minute structure portions such as the ejection ports, the flow channels communicating with these, and the like while also reducing attachment of the liquid to the ejection port surface 2*a* of the ejection element substrate 2.

Incidentally, there is also a case where, in the sterilization process, the sterilization target is not put in the sheet member but the sterilization target is directly placed in the vessel of the sterilization apparatus and high-pressure steam sterilization is performed. In this case too, in order for the sterilization target subjected to the sterilization process to maintain the sterilized state, the sterilization target needs to be sealed in a sterilized bag after being taken out of the vessel. However, performing the work of sealing the sterilization target while maintaining its sterilized state requires the sterilization target to be handled with meticulous care, which is troublesome and costly.

Also, one may consider a method in which tape or the like is attached to the ejection port surface of the ejection element substrate of the liquid ejection head in advance and that liquid ejection head is put into a sheet member and subjected to high-pressure steam sterilization. However, in the liquid ejection head, the ejection ports are minute, and the flow channels for supplying a liquid to the ejection ports are long in the depth direction. For this reason, each of the flow channels is one of the portions that is difficult to bring steam to. Thus, in the case where tape or the like is used to completely block inflow of steam from the ejection ports, it is possible to avoid attachment of a liquid to the ejection port surface, but the entrance for steam into the flow channels is limited to the side from which a liquid is filled. This makes it difficult to bring steam to the entire flow channels and therefore results in the liquid ejection head in a less sterilized state.

In the present embodiment, the ejection ports are not tightly closed. Accordingly, steam can be introduced from the opening portion side of the ejection ports. This makes it possible to bring the steam to the entire flow channels and therefore achieve a good sterilized state.

<Sterilization Step>

Figure 9:
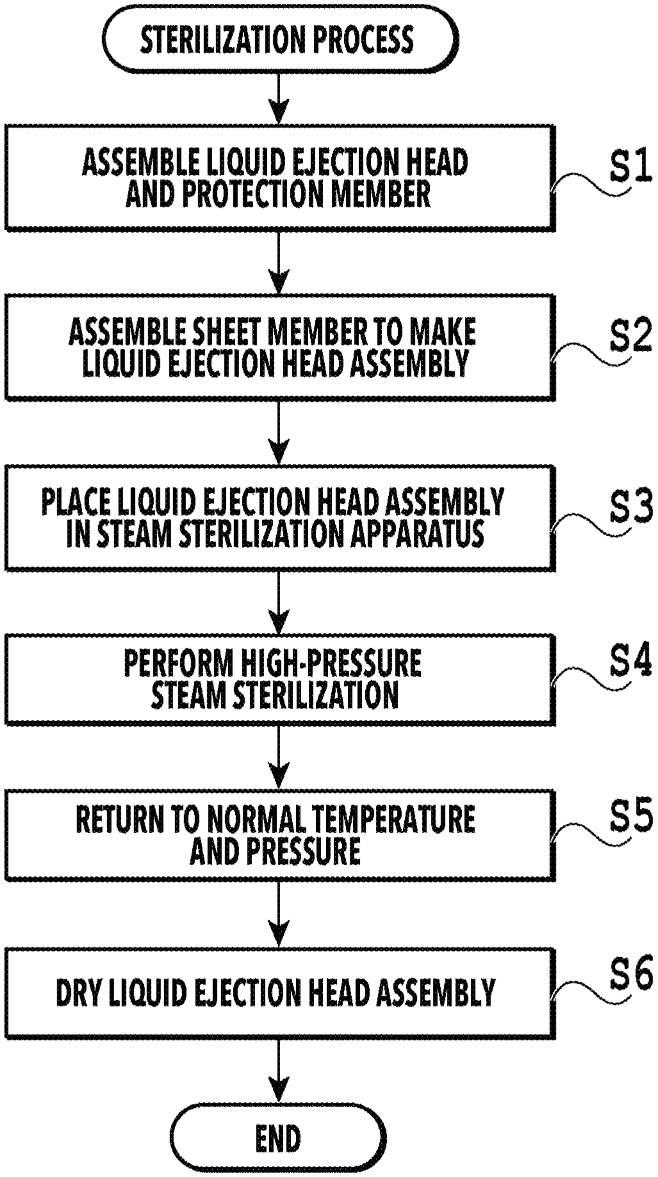
FIG. 9 is a flowchart illustrating a process procedure for performing a high-pressure steam sterilization process.

Now, a process procedure for performing a high-pressure steam sterilization process by using one of the liquid ejection head assemblies in the present embodiment will be described based on a flowchart in FIG. 9. Note that "S" attached to each process number in the flowchart in FIG. 9 means a step.

Firstly, the protection member 10A or 10B is assembled to the liquid ejection head 1 (S1 (first step)). Here, in the case of using the protection member 10A, the liquid ejection head 1 is housed in the protection member 10A. On the other hand, in the case of using the protection member 10B, the claws 10B4 and 10B5 of the protection member 10B are engaged with the housing 3 of the liquid ejection head 1 to thereby fix the protection member 10B to the housing 3. As a result, at least the ejection port surface 2*a* of the ejection element substrate 2 of the liquid ejection head 1 is covered with the protection member 10A or 10B.

Next, the sheet member 9A or 9B is further assembled to the structure obtained by assembling the liquid ejection head 1 and the protection member 10A or 10B to thereby make one of the liquid ejection head assemblies 11A to 11D (S2 (second step)). Here, in the case of using the bag-shaped sheet member 9A, the structure obtained by assembling the liquid ejection head 1 and the protection member 10A or 10B is sealed in that sheet member 9A. On the other hand, in the case of using the sheet member 9B, the sheet member 9B is bonded to the opening portion 10A1 of the protection member 10A by thermal welding or the like to seal the protection member 10A. Here, the protection members 10A and 10B are out of contact with the ejection port surface 2*a* of the ejection element substrate 2. Also, the ejection element substrate 2 is exposed to the atmosphere. Nonetheless, the liquid ejection head 1 is covered with the protection member 10A (or 10B) and the sheet member 9A (or 9B). Thus, even after sterilization, the liquid ejection head 1 can maintain the sterilized state.

Next, the one of the assemblies 11A to 11D with the liquid ejection head 1 is placed in the vessel of a steam sterilization apparatus (S3). Thereafter, the steam sterilization apparatus is driven to perform steam sterilization (S4 (third step)). In the present embodiment, high-pressure steam sterilization is performed. After the sterilization process is finished, the inside of the steam sterilization apparatus is returned to normal temperature and pressure (S5 (fourth step)), and the one of the liquid ejection head assemblies 11A to 11D is dried (S6 (fifth step)).

<Examples of Usage of Liquid Ejection Head after Sterilization Process>

The liquid ejection head after the sterilization process may be filled with a liquid subjected to a sterilization process in advance and eject the liquid. In this way, the ejected liquid can also maintain the sterilized state. For example, the liquid ejection head after the sterilization process may be filled with a liquid to be used in cell culture, and eject the liquid toward to a culture dish to which cells are attached. In this way, a cell suspension maintained in a sterilized state can be introduced onto the culture dish. In other words, the liquid ejection head after the sterilization process can be used as means for dispensing a predetermined amount of a sterilized liquid to a predetermined position.

The liquid ejection head after the sterilization process may be filled with a liquid containing cells in a dispersed state and eject the liquid toward a culture dish. In this way, the cells can be seeded on the culture dish. In other words, the liquid ejection head after the sterilization process can be used as means for moving a predetermined amount of cells to a predetermined position.

The liquid ejection head after the sterilization process may be filled with cells and a compound desired to be introduced into the cells and eject them. In this way, the compound can be introduced into the cells. In other words, the liquid ejection head after the sterilization process can be used as means for introducing a compound to cells.

EXAMPLES

The method of sterilizing the liquid ejection head shown in the above embodiment will be described more specifically with first to sixth examples and first and second comparative examples.

In the examples and comparative examples to be described below, a liquid ejection head assembly was made, and that assembly was subjected to high-pressure steam sterilization and then dried. Then, the examples and comparative examples were each evaluated by observing whether dried liquid marks (watermarks) were formed on the ejection element substrate.

In the present examples, two types of protection members 10A and 10B, two types of sheet members 9A and 9B, a lid 5, and a liquid ejection head 1 were assembled to make respective liquid ejection head assemblies. Also, in the comparative examples, the liquid ejection head 1 was sealed in the bag-shaped sheet member 9A to make respective assemblies with the liquid ejection head 1. Further, the sterilization process was performed with the temperature and time of the steam sterilization and the orientation of the ejection port surface 2*a* of the ejection element substrate 2 during the steam sterilization defined as the steam sterilization conditions. As the liquid ejection head 1, the liquid ejection head 1 illustrated in FIG. 1 (manufactured by Canon Inc.) was used. This liquid ejection head 1 is the inkjet print head to be used to eject a black ink that is mounted in the business inkjet printer G1310 manufactured by Canon Inc.

Table 1 shows the assembly configuration and the steam sterilization conditions in each of the examples and comparative examples, and the evaluation result of each example.

The protection member 10A shown in Table 1 is similar to the protection member 10A illustrated in FIGS. 4A and 5A and refers to a box-shaped protection member (manufactured by Canon Inc.). The protection member 10B in Table 1 is similar to the protection member 10B illustrated in FIGS. 7A and 7B and refers to a protection member (manufactured by Canon Inc.) that is fixable to the liquid ejection head. The sheet member 9A in Table 1 is similar to the sheet member 9A illustrated in FIGS. 4A and 5B and refers to a bag-shaped sheet member (simple sterilization pouch manufactured by Thermo Fisher Scientific K.K.). The sheet member 9A is made of a vapor-permeable sterile paper, polypropylene, polyethylene terephthalate, or the like. The sheet member 9A is provided with tape for closing its opening portion 9A1 after a sterilization target is put therein. The sheet member 9B is similar to the sheet member 9B illustrated in FIG. 6A and is made of a polyethylene non-woven fabric sheet (Tyvek (registered trademark) manufactured by DuPont).

In the first example, the liquid ejection head 1 was housed in the box-shaped protection member 10A. Next, the protection member 10A housing the liquid ejection head 1 was put in the bag-shaped sheet member 9A. Lastly, the opening portion 9A1 of the bag-shaped sheet member 9A was closed with the tape provided on the sheet member 9A. As a result, a liquid ejection head assembly 11A was made. A cross-sectional view of this assembly 11A is similar to FIG. 4A.

In the second example, the protection member 10B (see FIG. 7B) was fixed to the liquid ejection head 1. Next, the liquid ejection head 1 with the protection member 10B attached thereto was put in the bag-shaped sheet member 9A. Lastly, the opening portion 9A1 of the bag-shaped sheet member 9A was closed with the tape provided on the sheet member 9A. As a result, a liquid ejection head assembly 11D was made. A cross-sectional view of this assembly 11D is similar to FIG. 7A.

In the third, fourth, and fifth examples, the liquid ejection head 1 was housed in the box-shaped protection member 10A. Further, the opening portion of the housing 3 of the liquid ejection head 1 was covered with the lid 5. Next, the protection member 10A housing the liquid ejection head 1 and the lid 5 was put in the bag-shaped sheet member 9A. Lastly, the opening portion 9A1 of the bag-shaped sheet member 9A was closed with the tape provided on the sheet member 9A. As a result, a liquid ejection head assembly 11C was made. A cross-sectional view of this assembly is similar to FIG. 6B.

In the sixth example, the liquid ejection head 1 and the lid 5 were put in the box-shaped protection member 10A. Next, the sheet member 9B was placed on the opening portion of the box-shaped protection member 10A, and the sheet member 9B was fixed to the protection member 10A by thermal welding. As a result, a liquid ejection head assembly was made. In other words, in this assembly, the opening portion of the protection member is covered with the sheet member. A cross-sectional view of this assembly is similar to FIG. 6A except that the lid 5 is not illustrated.

In the first and second comparative examples, the liquid ejection head was put in the bag-shaped sheet member 9A, and the opening portion 9A1 of the bag-shaped sheet member 9A was closed with the tape provided on the sheet member 9A. As a result, a liquid ejection head assembly 11 was made. A cross-sectional view of this assembly is similar to FIG. 3A. Note that the sheet member 9 illustrated in FIGS. 3A and 3B is similar to the bag-shaped sheet member 9A illustrated in FIG. 5B.

Next, steam sterilization was performed on the assemblies in the first to sixth examples and the first and second comparative examples by using a steam sterilization apparatus (MX-500 (manufactured by TOMY SEIKO CO., LTD.)). The steam sterilization conditions in the examples and comparative examples are described in Table 1. Note that in the steam sterilization, the assembly was put in a basket and the assembly in this state was placed in the vessel of the steam sterilization apparatus. The assembly was placed with the ejection port surface 2*a* of the ejection element substrate 2 facing down or up in the direction of gravity. Specifically, the assembly was placed with the ejection port surface 2*a* facing up in the first to fourth and sixth examples and the second comparative example, whereas the assembly was placed with the ejection port surface 2*a* facing down in the fifth example and the first comparative example.

Also, the steam sterilization apparatus was used to perform steam sterilization at a temperature of 121° C. for 20 minutes or at a temperature of 134° C. for 15 minutes. Specifically, steam sterilization was set to be performed at a temperature of 121° C. for 20 minutes in the first to third and sixth examples and the first and second comparative examples, whereas steam sterilization was set to be performed at a temperature of 134° C. for 15 minutes in the fourth and fifth examples.

After the steam sterilization apparatus presented a display indicating the end of the sterilization, the basket was taken out of the steam sterilization apparatus. The assembly, kept in the basket, was put in a dryer and dried at 60° C. for four hours or longer. After the drying, the liquid ejection head 1 was taken out of the assembly. With a metallograph, the ejection port surface 2*a* of the ejection element substrate 2 was observed to check whether dried liquid marks were present. Based on whether dried liquid marks were present, a determination was made based on A: there was no dried liquid mark, B: there were a very few dried liquid marks, and C: there were many dried liquid marks as an evaluation result.

The elements of each assembly used in the above sterilization process were as follows.

Liquid ejection head: approximately 50×30×30 mm (manufactured by Canon Inc.)

Lid: manufactured by Canon Inc.

Protection member 10A: approximately 60×35×40 mm (manufactured by Canon Inc.)

Protection member 10B: manufactured by Canon Inc.

Sheet member 9A: bag-shaped sheet (simple sterilization pouch, approximately 130×250 mm (manufactured by Thermo Fisher Scientific K.K.))

Sheet member 9B: non-woven fabric sheet (Tyvek (manufactured by DuPont Company))

In the assembly 11A, the protection member 10A having a hollow box shape can support the liquid ejection head 1 with the support portion 10A2 provided at the bottom. Thus, even with the liquid ejection head 1 housed in the protection member 10A, the ejection element substrate 2 and the protection member 10A did not contact each other. Also, the exterior size of the liquid ejection head 1 was approximately 50×30×30 mm, the exterior size of the protection member 10A was approximately 60×35×40 mm, and the size of the bag-shaped sheet member 9A was approximately 130×250 mm. This made it possible to seal the opening portion 9A1 of the sheet member 9A with the tape provided thereon after the protection member 10A with the liquid ejection head 1 put therein was housed in the sheet member 9A. Also, since the protection member 10A housing the liquid ejection head 1 was covered with the bag-shaped sheet member 9A, the liquid ejection head 1 did not come out of the protection member 10A of the hollow box shape and the state where the liquid ejection head 1 was inside the protection member 10A could be maintained. An indicator that changes its color by being subjected to steam sterilization was attached to the bag-shaped sheet member 9A. After the steam sterilization process, it was confirmed that the color of the sheet member changed.

Figure 10:
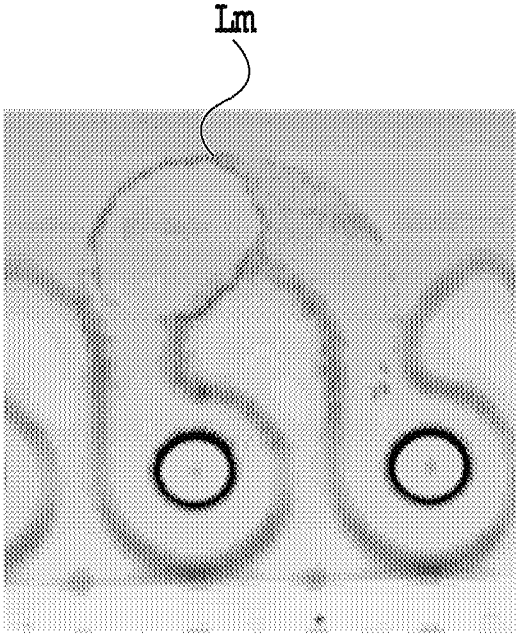
FIG. 10 is a view illustrating a dried liquid mark formed on the ejection element substrate.

In the first and second comparative examples, as illustrated in FIG. 10, dried liquid marks Lm formed as a result

TABLE 1

| | | First Example | Second Example | Third Example | Fourth Example | Fifth Example | Sith Example | First Comparative Example | Second Comparative Example |
|---|---|---|---|---|---|---|---|---|---|
| Assembly | Liquid Ejection Head | Included | Included | Included | Included | Included | Included | Included | Included |
| | Lid 5 | Not Included | Not Included | Included | Included | Included | Included | Not Included | Not Included |
| | Protection Member 10A/10 B | 10A | 10B | 10A | 10A | 10A | 10A | Not Included | Not Included |
| | Sheet Member 9A/9B | 9A | 9A | 9A | 9A | 9A | 9A | 9B | 9A |
| Steam Sterilization | Temperature and Time | 121° C. 20 min | 121° C. 20 min | 121° C. 20 min | 121° C. 20 min | 134° C. 15 min | 134° C. 15 min | 121° C. 20 min | 121° C. 20 min |
| Conditions | Orientation of Ejection Element Substrate | Up | Up | Up | Up | Down | Up | Down | Up |
| Evaluation Result | Dried Liquid Marks | A | A | A | A | B | A | C | C |

of drying a liquid attached to the ejection element substrate 2 were found on the ejection port surface of the ejection element substrate 2. In the fifth example, dried liquid marks were locally found, but the dried liquid marks were formed less frequently than the first and second comparative examples. Also, even in the case where dried liquid marks were formed, the region where they were formed was so small that they did not cause ejection failure of the liquid head. In the first to fourth and sixth examples, no dried liquid mark was found. As described above, it is clear that using the protection members 10A and 10B can reduce formation of dried liquid marks on the ejection port surface 2*a*.

Next, whether the liquid ejection head was properly sterilized by the high-pressure steam sterilization process was checked by using a biological indicator for vapor sterilization (H3723T (Fukuzawa Shoji Kabushiki kaisha). In order to check the sterilized state by using this biological indicator, when the liquid ejection head assembly was made, the biological indicator was put in the liquid storage part 3*a* of the housing 3 in advance, and the opening portion of the liquid storage part 3*a* was tightly closed with the lid 5. The lid 5 was fixed to the liquid storage part 3*a* by welding.

Next, that liquid ejection head 1 was housed in the protection member 10A, and that protection member 10A was put in the bag-shaped sheet member 9A (manufactured by DuPont Company). Thereafter, the opening portion 9A1 of the sheet member 9A was closed by thermal welding. As a result, an assembly 11C was made. A cross-sectional view of the assembly 11C is similar to FIG. 6B. This assembly 11C was placed in the steam sterilization apparatus with the ejection port surface 2*a* of the ejection element substrate 2 facing up, and steam sterilization was performed at a temperature of 134° C. for 15 minutes. After the end of the sterilization, the biological indicator for vapor sterilization was taken out without performing a drying step, and heated to 56° C. 48 hours later, whether sterilization had been done was checked from the change in the color of the biological indicator for vapor sterilization. Incidentally, 56° C. is a suitable temperature for bacterial culture, and 48 hours is the time for bacterial culture. In a case where bacteria were present even after the steam sterilization process, those bacteria would be cultured and the color of the biological indicator would change.

After the elapse of 48 hours, the color of the biological indicator for vapor sterilization was checked. The result was that the color of the biological indicator was purple, indicating that sterilization had been done. In the assembly 11C used in the checking of the sterilized state, the opening portion of the liquid storage part 3*a* of the liquid ejection head 1 was tightly closed with the lid 5, so that the entrance for steam into the flow channels 7 is limited to the ejection ports 6. Thus, in a case where the color of the biological indicator inside the liquid storage part 3*a* changes as described above after the steam sterilization process, it is proof that steam has successfully flowed in from the ejection ports 6 and been filled in the liquid storage part 3*a* through the flow channels 7. In other words, it is proof that the liquid storage part 3*a*, the liquid outlet port 3*b*, the liquid supply port 21*a*, the flow channels 7, and the ejection ports 6 have been successfully sterilized. In this example, the color of the biological indicator changed to purple. This makes it clear that a sterilization process has been properly performed on the ejection ports 6 and the flow channels 7, which are the most difficult portions to sterilize in the liquid ejection head.

Next, whether the liquid ejection head after the sterilization process maintained proper ejection performance was checked. Firstly, the liquid ejection head 1 was housed in the protection member 10A. Next, the protection member 10A housing the liquid ejection head 1 was put in the bag-shaped sheet member 9A, and the opening portion 9A1 of that sheet member 9A was closed, so that an assembly was made. A cross-sectional view of the assembly is similar to FIG. 4A. This assembly 11A was placed in the steam sterilization apparatus with the ejection port surface 2*a* of the ejection element substrate 2 facing up, and steam sterilization was performed at a temperature of 134° C. for 15 minutes. After the end of the sterilization, the assembly was moved out of the steam sterilization apparatus into the dryer with the ejection port surface 2*a* kept facing up, and was dried at a temperature of 60° C. for four hours or longer. The liquid ejection head 1 was taken out of the assembly 11A, and the ejection port surface 2*a* of the ejection element substrate 2 was observed with a metallograph. Moreover, a liquid (black ink (product name: GI-390BK), manufactured by Canon Inc.) was filled into the liquid ejection head, and the liquid was ejected with a liquid ejection apparatus (inkjet printer (product name: G1310), manufactured Canon Inc.).

In the sterilized liquid ejection head 1, no cracking or detachment of the ejection element substrate 2 was found. Moreover, no dried liquid mark or foreign object was found on the ejection element substrate 2. As a result of ejecting the liquid with the liquid ejection apparatus, a sterilized liquid was ejected. The liquid was ejected from almost all ejection ports 6 formed in the ejection element substrate 2. This result has made it clear that, in the case of steam-sterilizing the liquid ejection head 1 with the assembly 11A using the protection member 10A, formation of dried liquid marks on the ejection port surface 2*a* of the ejection element substrate 2 can be inhibited, and the occurrence of ejection failure can therefore be inhibited. In other words, the liquid ejection head was able to maintain proper ejection performance even after being subjected to the high-pressure steam sterilization process.

Second Embodiment

In the present embodiment, a description will be given of a configuration in which the ejection apparatus is used as a compound introduction apparatus that introduces a compound into cells. The liquid ejection head 1 is filled with a liquid containing a compound and cells into which the compound is to be introduced. In the present embodiment, this liquid will be referred to as "cell suspension" (also called "cell-containing liquid"). The liquid ejection head 1 may be called "cell processing head". The cell suspension after being ejected from the liquid ejection head 1 contains cells into which the compound has been introduced. In the following description, the compound to be introduced into cells will also be referred to as "introduction-target compound".

<Introduction-Target Compound>

The compound to be introduced can be selected as appropriate according to its purpose. Conceivable examples of introducible compounds include nucleic acids, proteins, labeling substances, and the like. Note that the compound is not limited to these examples as long as it is a compound of such a size as to be containable within a cell into which it is to be introduced. However, in view of minimizing damage to the cells, the size of the compound is preferably ⅕ of the average diameter of the cells or smaller, and more preferably 1/10 of the average diameter of the cells or smaller. Representative compounds that can be employed in the present embodiment include nucleic acids such as DNA and RNA.

<Cell Types>

Cells to be handled in the present embodiment include adherent cells, suspension cells, spheroids (cell aggregates), and the like. The average diameter of the cells is such that a cell can be ejected from an ejection port and is, for example, 1 μm or more and 100 μm or less.

<Cell Suspension>

The cell suspension has at least one introduction-target compound to be introduced and one or more cells into which the introduction-target compound is to be introduced and contains water as its main component. Further, in the present invention, the cell suspension is a liquid in which cells are dispersed. The cells in the cell suspension have only to be in a state in which the cells can be dispersed in the liquid by agitating, and may be precipitated in the liquid in a case where the cell suspension is kept in a stationary state. Incidentally, other components are preferably contained as appropriate so that the cells can survive during introduction processing and after it.

<Water and Water-Soluble Organic Solvent>

The cell suspension to be handled in the present embodiment can use an aqueous liquid medium containing water or a mixture of water and a water-soluble organic solvent. The cell suspension can be obtained by adding the cells and the introduction-target compound to the aqueous liquid medium.

<Compound Introduction Method>

In a compound introduction method in the present embodiment, cells cultured by adherent culture, suspension culture, or the like are separated into single cells or small cell aggregates via an action of an enzyme or the like and then, with a centrifuge or the like, only the cells are caused to settle by utilizing the difference in relative density. Thereafter, the supernatant medium excluding the cells is removed, and then the medium containing the introduction-target compound is added followed by agitation with a pipette or an agitator. As a result, a cell suspension is prepared.

The prepared cell suspension is passed through a cell strainer having substantially the same diameter as the smallest diameter of the flow channels in the liquid ejection head 1 to be used, to thereby exclude large cell aggregates. The cell suspension thus prepared is introduced into the liquid ejection head 1 by using a micropipette or the like. In a case where the cell suspension is smoothly filled to the ejection ports 6 of the liquid ejection head 1 with wetting and spreading of the cell suspension due to surface tension, the introduction operation is executed as soon as the cell suspension is filled. In a case where the cell suspension cannot be filled to the ejection ports 6 of the liquid ejection head 1, the cell suspension can be filled via suction from the ejection ports 6 with a suction mechanism or an external suction pump. Alternatively, the cell suspension can be filled by pressurizing the liquid storage part 3*a* holding the cell suspension therein with an external pressurization pump.

Thereafter, the compound is introduced into the cells by driving the ejection energy generation elements (ejection elements) in the liquid ejection head 1. Then, the cell suspension is ejected from the ejection ports 6 into a base material or culture medium. The introduction-target compound has been introduced into the ejected cells.

The following shows the result of considering whether the performance of introducing a compound into cells differs between a liquid ejection head with a sterilization process and a liquid ejection head without a sterilization process.

The liquid ejection head 1 and the lid 5 were housed in the protection member 10A, and that protection member 10A was put in the bag-shaped sheet member 9A (manufactured by DuPont Company). Thereafter, the opening portion of the sheet member 9A was closed by thermal welding. As a result, the assembly 11C was made. Steam sterilization was performed at a temperature of 126° C. for 15 minutes. After the end of the sterilization, the assembly 11C was dried naturally.

Cells derived from a Chinese hamster ovary (CHO-K1, manufactured by Cellular Engineering Technologies Inc.) were detached from a culture dish by using trypsin. After centrifugation, the supernatant was removed followed by dispersion in Ham's F-12 Nutrient Mix (F-12, manufactured by Thermo Fisher Scientific K.K.). Fluorescein isothiocyanate-dextran (FITC-Dex, molecular weight: 70 k, manufactured by Sigma-Aldrich Co. LLC), which was fluorescently labeled dextran, was dissolved in phosphate-buffered saline (PBS) at a concentration of 10 mg/ml. The CHO-K1 cell and FITC-Dex liquids were mixed to prepare a liquid containing CHO-K1 cells at a concentration of $2.0\times10^6$ cells/ml and FITC-Dex at a concentration of 0.5 mg/ml. The prepared liquid was filled into the liquid ejection head after the sterilization process and the liquid ejection head without the sterilization process. With the liquid ejection apparatus, each filled liquid was ejected toward a culture dish (Glass Base Dish, manufactured by AGC TECHNO GLASS CO., LTD.). Cells were observed using a phase-contrast microscope. Thereafter, an F-12 culture medium containing 10% fetal bovine serum (FBS) and 1% penicillin-streptomycin was added followed by observation with the phase-contrast microscope. After two hours of incubation under a 37° C.-temperature and 5%-$CO_2$ environment, the cells were detached using trypsin and centrifuged. The supernatant was removed, and then the cells were dispersed again in PBS containing 2% FBS. By using a cell sorter (BD FACSMelody cell sorter, manufactured by Nippon Becton Dickinson Co., Ltd.), the amount of the FITC-Dex introduced into the CHO-K1 cells was measured. The cell sorter performed the measurement under conditions of laser: 488 nm, mirror: 507LP, and filter: 527/32, with which the FITC could be detected, and performed an analysis by gating the cell distribution from data on forward scatter and side scatter.

Figure 11:
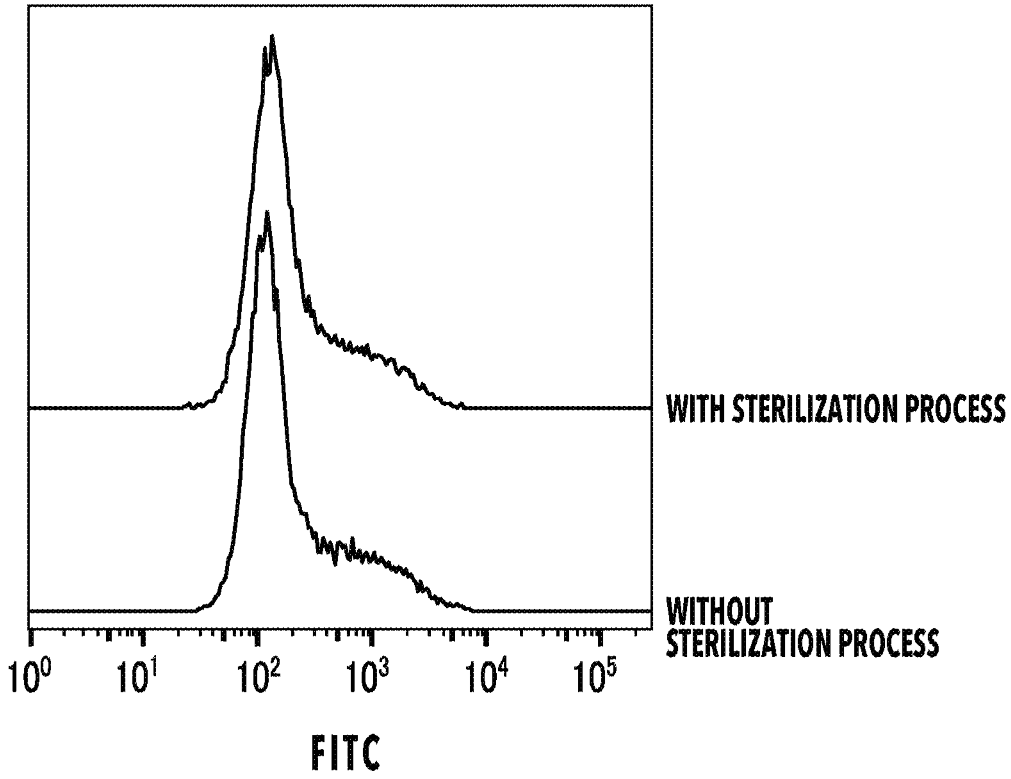
FIG. 11 is a diagram illustrating how performing a sterilization process and performing no sterilization process affect cells in a liquid ejection head.

As a result of making an observation with the phase-contrast microscope, it was found that cells were ejected from both the liquid ejection head with the sterilization process and the liquid ejection head without the sterilization process. As a result of making an observation with the phase-contrast microscope after adding the F-12 culture medium, many white-glowing cells were found among both the cells ejected from the liquid ejection head with the sterilization process and the cells ejected from the liquid ejection head without the sterilization process. FIG. 11 shows the result of the analysis by the cell sorter. It is a histogram with a horizontal axis representing the intensity ratio of the FITC and a vertical axis representing the count. The amount of the FITC-Dex taken into the CHO-K1 cells did not greatly differ between the liquid ejection head with the sterilization process and the liquid ejection head without the sterilization process. The liquid ejection head with the sterilization process maintained its performance on cells for introducing the compound into cells.

Other Embodiments

Note that in the above embodiments, examples in which a liquid ejection head to be subjected to steam sterilization is used to eject a cell suspension. However, the present disclosure is also applicable to liquid ejection heads that eject a liquid which needs to be sterilized before being ejected.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2021-044711 filed Mar. 18, 2021 and No. 2022-037248, filed Mar. 10, 2022, which are hereby incorporated by reference wherein in their entirety.

What is claimed is:

1. A method of sterilizing a liquid ejection head including an ejection element substrate that has an ejection port surface in which an ejection port for ejecting a liquid is formed, and a liquid storage part that stores the liquid to be supplied to the ejection port, the method comprising the steps of:

covering at least the ejection port surface of the liquid ejection head with a protection member in a non-contact manner;

making a liquid ejection head assembly by:

housing the protection member and the liquid ejection head in a first sheet member having a bag shape, the first sheet member being vapor permeable at least at one portion in such a manner as to block entry of bacteria into the liquid ejection head, in a state where the first sheet member is out of contact with the ejection port surface; or housing the liquid ejection head in a space formed by covering an opening portion of the protection member with a second sheet member, where the second sheet member is vapor permeable at least at one portion in such a manner as to block entry of bacteria into the liquid ejection head, in a state where the second sheet member is out of contact with the ejection port surface; and performing vapor sterilization on the assembly.

2. The method according to claim 1, further comprising cooling the assembly after the vapor sterilization.

3. The method according to claim 1, wherein the Young's modulus of the protection member is 1 to 100 MPa.

4. The method according to claim 1, wherein the protection member has a hollow box shape in which is formed the opening portion that enables the liquid ejection head to be housed in the protection member and put into and out of the protection member, and covers the ejection port surface of the liquid ejection head housed in the protection member with a predetermined interval therebetween.

5. The method according to claim 4, wherein the protection member has a bottom surface portion covering the ejection port surface of the liquid ejection head housed in the protection member, and a support portion supporting the liquid ejection head with the bottom surface portion separated from the ejection port surface.

6. The method according to claim 4, wherein the second sheet member is fixed to the protection member in such a manner as to cover the opening portion.

7. The method according to claim 1, wherein the first sheet member has such a peripheral length as to prevent the liquid ejection head from coming out of the protection member from the opening portion thereof.

8. The method according to claim 1, wherein the protection member has an engagement portion engageable with the liquid ejection head, and a covering portion detachably fixed to the liquid ejection head by the engagement portion and covering the ejection port surface in a state of being fixed to the liquid ejection head.

9. The method according to claim 1, wherein the vapor sterilization is performed on the assembly in a state where the assembly is placed with the ejection port surface facing up.

10. The method according to claim 1, wherein the vapor sterilization is performed on the assembly in a state where the assembly is placed with the ejection port surface facing down.

11. The method according to claim 1, wherein the assembly includes a lid that detachably closes an opening portion formed in the liquid storage part.

12. The method according to claim 1, wherein the vapor sterilization is steam sterilization.

13. The method according to claim 1, wherein the vapor sterilization is high-pressure steam sterilization performed using an autoclave at a pressure of from atmospheric pressure+0.1 MPa to atmospheric pressure+0.2 MPa.

* * * * *